US00PP10440P

United States Patent [19]

Ebihara

[11] Patent Number: Plant 10,440

[45] Date of Patent: Jun. 9, 1998

[54] HYDRANGEA PLANT NAMED 'FRAU FUJIYO'

[75] Inventor: Hiroshi Ebihara, Ninomiya-machi, Japan

[73] Assignee: Miyoshi & Co. Ltd., Tokyo, Japan

[21] Appl. No.: 733,333

[22] Filed: Oct. 17, 1996

[51] Int. Cl.[6] ..... A01H 5/00

[52] U.S. Cl. ..... Plt./67.1

[58] Field of Search ..... Plt./67.1

[56] References Cited

U.S. PATENT DOCUMENTS

| | | | |
|---|---|---|---|
| P.P. 9,499 | 4/1996 | Ebihara | Plt./67.1 |
| P.P. 9,500 | 4/1996 | Ebihara | Plt./67.1 |
| P.P. 9,510 | 4/1996 | Ebihara | Plt./67.1 |

OTHER PUBLICATIONS

UPOVROM Disk 1997/03 ① Result Sheet 1 GTITM UPOV/ROM Listing NL PBR HDG0018 published Jul. 16, 1994 1997.

UPOVROM Disk 1997/03 ② Result Sheet 2 GTITM UPOV/ROM Listing N2 PBR SHM092 published Jul. 14, 1996 1997.

UPOVROM Disk 1997/03 ③ Result Sheet 3 GTITM UPOV ROM Listing AU PBR 96117 filing date May 31, 1996 1997.

*Primary Examiner*—James R. Feyrer
*Assistant Examiner*—Kent L. Bell
*Attorney, Agent, or Firm*—James R. Cypher

[57] ABSTRACT

This invention relates to a new and distinct cultivar of *Hydrangea macrophylla* (Thunb.) named 'Frau Fujiyo' which originated as a seedling from the inventor's controlled hybridization of the *Hydrangea macrophylla* cultivars 'Madam Blumkock' and 'Silver Edge' and is distinguished from its parents and all other varieties of *Hydrangea macrophylla* of which I am aware by the combination of the distinctive pigmentation pattern of its sepals which gives the florets a pin-wheel appearance; its compact growth habit; the ease with which it can be forced in a greenhouse; and its large, dense, long-lasting inflorescence having a strong peducnle which does not require staking for support, making it ideal for pot culture. Sepal pigmentation of individual *Hydrangea macrophylla* plants depends on the nutrients and pH of the growing medium. The sepals of 'Madam Blumkock' are uniformly pink and the sepals of 'Silver Edge' are uniformly red with a white edge.

1 Drawing Sheet

BACKGROUND OF THE INVENTION

This invention relates to a new and distinct cultivar of the *Saxifragaceae* family. The botanical name of the plant is *Hydrangea macrophylla* (Thunb.). The varietal denomination is 'Frau Fujiyo'. The new cultivar originated as a seedling from the inventor's controlled crossing as pollen and seed parents, respectively, the varieties known as 'Madam Blumkock' and 'Silver Edge' in Tochigi-Prefecture, Japan. 'Frau Fujiyo' was discovered and selected as one flowering plant within the progeny of the stated parentage in a controlled environment.

'Frau Fujiyo' is distinguished from its parents and all other varieties of *Hydrangea macrophylla* of which I am aware, by the combination of the distinctive pigmentation pattern of its sepals which gives the florets a pin-wheel appearance; its compact growth habit; the ease with which it can be forced in a greenhouse; and its large, dense, long-lasting inflorescence having a strong peduncle which does not require staking for support, making it ideal for pot culture.

The naturally occurring colors of Hydrangea plants are either uniformly pink, blue or white depending on the pH and nutrients of the soil. Hydrangea plants having mixed white and pink or white and blue flower coloring are relatively new and not in common use. The sepal color of 'Frau Fujiyo' begins uniformly green and turns color starting at the outer tips of the sepals, and at maturity is predominantly colored with an irregular, white edge. As each floret matures, the color starts in the tip of the green sepal, and simultaneously the color in the tip spreads down the center of the sepal and slowly spreads out towards the sides while the green color turns to white, resulting in each sepal having color the length of the center of the sepal and white sides. This gives each floret the appearance of a pin-wheel, and the inflorescence appears to be composed of a multitude of pin-wheel florets. This pin-wheel effect lessens as the inflorescence ages and the color spreads out more to the sides, but it can be seen again in the very old blooms that develop chlorophyll as they fade and die. The sepal coloration of the seed parent 'Silver Edge' is uniformly red with a white edge, and the sepal coloration of the pollen parent 'Madam Blumkock' is uniformly pink.

This new cultivar has been successfully asexually reproduced by vegetative cuttings under controlled environmental conditions at a commercial nursery in Tochigi-Prefecture, Japan, under the direction of the inventor over a ten year period from 1986 to 1996, with its distinguishing characteristics remaining stable.

DESCRIPTION OF THE DRAWINGS

The accompanying drawings consist of color photographs that show the typical plant form, including the inflorescence, foliage, and unique sepal pigmentation pattern. 'Frau Fujiyo' is shown with a pink and white sepal pigmentation pattern, but a blue and white pigmentation pattern is also possible by manipulation of the nutrient amendments and the pH of the growing meidum. The colors are represented as truly as possible using conventional photographic procedures.

DESCRIPTION OF THE NEW PLANT

Figure 1:
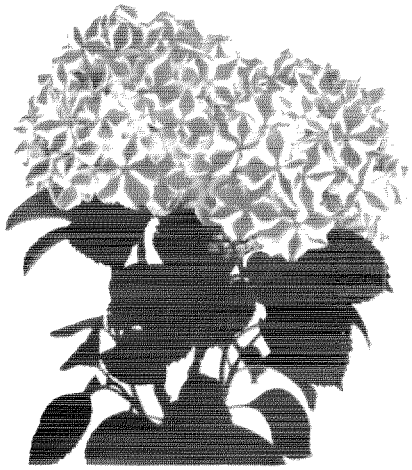
FIG. 1 is a view of the entire plant showing its form, compact growth habit, dark green foliage, dense and large inflorescence, and unique pin-wheel-like sepal pigmentation pattern.
Figure 2:
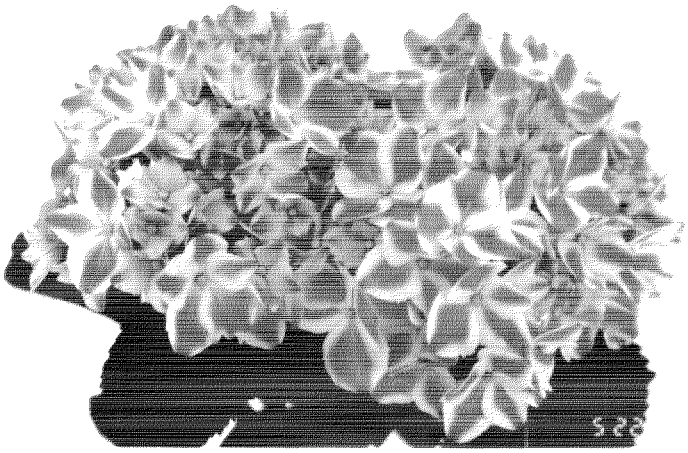
FIG. 2 is a close-up view of a flower head illustrating the stages of the color changes occurring in the sepals as they mature.
Figure 3:
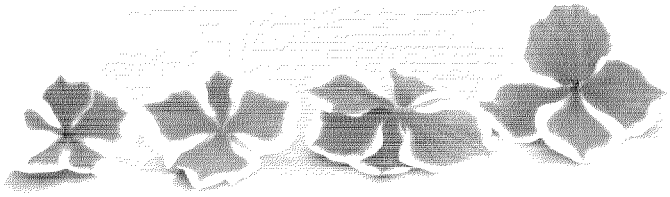
FIG. 3 is a close-up-view of four individual florets at maturity illustrating the flat, overlapping shape of the sepals, the irregular white edges with color in the center of the sepals spreading lengthwise to the apex, and the irregularly serrated edges of the sepals.

'Frau Fujiyo' has not been observed under all possible environmental conditions. The phenotype may vary significantly with variations in environment such as temperature, light intensity and day-length. The following is a detailed description of the new cultivar as forced under the prevailing day-lengths at Half Moon Bay, Calif. under commercial greenhouse conditions at a time appropriate for the sale of the cultivar in the spring. The color determinations were made with The Royal Horticultural Society (R.H.S.) Colour Chart.

THE PLANT

Origin: Seedling.

Parentage:

*Seed parent.*—*Hydrangea macrophylla* (Thunb) 'Silver Edge'.

*Pollen parent.*—*Hydrangea macrophylla* (Thunb) 'Madam Blumkock'.

Classification:

*Botanic.*—*Hydrangea macrophylla* (Thunb.) 'Frau Fujiyo'.

*Commercial.*—Florist Hydrangea 'Frau Fujiyo'.

Form: Upright, compact shrub.

Height: Flowering shoots reach 28 cm. in a 4" pot.

Growth: Upright, vigorous growth habit; when forced to bloom in greenhouse the addition of growth regulators is necessary to control height.

Flowerhead: Terminal; composite, rounded clusters of small florets; dome-shaped and dense; composed of florets carried on sturdy peduncles.

Stems: Lenticels are reddish on the stem; lateral buds are reddish; reddish coloration above leaf attachments sites.

Foliage: Abundant.

*Size of leaf.*—As large as 76 mm wide by 84 mm long.

*Shape of leaf.*—Elliptic with acute base and apex; margins are serrate.

*Texture.*—Glabrous; veins dominate on the underside of the leaf and are sunken on the leaf surface.

*Color.*—Upper side is R.H.S. 137 A (green group); under side is R.H.S. 137 C (green group); veins are R.H.S. 145 C (yellow-green group).

*Petioles.*—24 mm long.

THE BUD

Form: Globose; with 4 to 5 connate petals. Buds in the very center of the inflorescence are non-sepalous. The majority of buds have sepals.

Size: 3 mm.

Aspect: Smooth.

Rate of opening: Buds with sepals opening more slowly than buds without sepals.

Color: Mature stage is R.H.S. 70B red purple group.

Arrangement: Borne on 4 to 5 branched panicles, usually 5.

INFLORESCENCE

Time of blooming: Forced in approximately 80 days at 19° C. night temperatures.

Form: Paniculate. Both sterile, sepalous florets and fertile, non-sepalous florets borne on same panicle.

Size of Inflorescence: Individual inflorescence size is dependent on the number of inflorescences per plant. The large inflorescences have been measured with a 15.25 cm diameter, and a 45.75 cm. circumference on a 4 bloom plant.

Shape: Spherical clusters of small florets; sepalous florets are flat and overlap one another. Sepals are persistent. Sepals elongate and mature as the inflorescence matures. Non-sepalous, are inconspicuous and hidden by sepalous florets. The inflorescence is dense.

Appearance: Showy.

Persistence: 4 or more weeks.

Fragrance: Faintly sweet.

Fruit: None.

Reproductive organs:

*Stamens.*—8 present. Pollen is white.

*Stigma.*—2 to 3 pronged stigma.

Sepalous florets:

*Number of sepals.*—4 to 5 sepals per floret, usually 4.

*Aspect of sepals.*—smooth.

*Shape of sepals.*—reniform with acuminate apex; edges often irregularly serrate.

*Size of sepals.*—usually one large dominate sepal; two smaller but of equal size, and one small. Largest single sepal measured 35 mm wide by 30 mm long.

*Size of one large 4 petaled floret.*—51 mm. wide by 49 mm. long.

*Coloration of sepals.*—Sepal color varies according to the soil pH and nutritional amendments supplied. Predominately pink or blue with an irregular white edge from 3 to 7 mm wide. Usually 3–5 mm wide; amount of white edge varies depending on the age of the flower and sepal location within the flower; Pink Flower: R.H.S. red purple group 63B. Edge: R.H.S. white group 155D.

I claim:

1. A new and distinct hybrid plant variety of the *Saxifragaceae* family substantially as herein shown and described.

* * * * *